United States Patent [19]

Gordon

[11] Patent Number: 4,470,408

[45] Date of Patent: Sep. 11, 1984

[54] GRAVITY TRACTION AND EXERCISE APPARATUS

[76] Inventor: Donald W. Gordon, 6061 Candlelight La., Yorba Linda, Calif. 92686

[21] Appl. No.: 386,516

[22] Filed: Jun. 9, 1982

[51] Int. Cl.³ .............................................. A61F 5/00

[52] U.S. Cl. ...................................... 128/71; 272/145

[58] Field of Search ................... 128/71, 25 R, 24, 75; 272/145, 144, 93, 62, 63

[56] References Cited

U.S. PATENT DOCUMENTS

| | | | |
|---|---|---|---|
| 1,693,810 | 12/1928 | Daniels | 272/144 |
| 2,895,736 | 7/1959 | Adler | 272/145 |
| 3,286,708 | 11/1966 | Gartner | 272/145 |
| 3,519,268 | 7/1970 | McQueen | 272/144 |
| 3,735,979 | 5/1973 | Levenberg | 272/144 |
| 3,857,561 | 12/1974 | Cecchettini | 272/144 |
| 3,874,375 | 4/1975 | Penner | 272/63 |
| 3,891,207 | 6/1975 | Helliwell | 272/144 |
| 4,114,613 | 9/1978 | Kuhn | 128/71 |
| 4,232,662 | 11/1980 | Barber | 128/71 |

*Primary Examiner*—Richard J. Johnson

*Attorney, Agent, or Firm*—Knobbe, Martens, Olson & Bear

[57] ABSTRACT

The gravity traction and exercise apparatus is a tall framework cuboid structure having a series of hand grips along one side and a foot ladder ascending the opposite side. At the top of the structure are two foot binders, each of which is a padded inverted L-shaped plate. The vertical portions of the two foot binders oppose one another to grasp the user's ankles between them. One foot binder is mounted on an inclined track so it can be moved from a lower position near the other foot binder up the track to an upper position away from the other foot binder, opening a space between the two foot binders through which the user's feet may be inserted. Once the user's feet and ankles are between the foot binders the insteps of the user's feet are placed against the top of the movable foot binder and the user's weight is used to pull the movable foot binder down the track to press against his ankles and securely hold them between the two foot binders. The padded binders that are under the user's insteps and pressing against his ankles prevent the user from slipping through the device.

10 Claims, 7 Drawing Figures

GRAVITY TRACTION AND EXERCISE APPARATUS

BACKGROUND OF THE INVENTION

Some time ago the benefits of exercising a person's body while the body is in an inverted position, with the head down, were publicized. With the body in an inverted position, some of the compression of the internal organs caused by gravity can be counteracted. Additionally, when the body is hung by the feet and ankles in an inverted position, the body can assume a more natural posture than is possible when a person is standing or sitting. This improved posture is particularly beneficial for the back. Further, when the body is inverted, certain exercises can be performed that are not possible when the body is in an upright position.

One device that has been developed for inverting the body for the purpose of stretching it and gaining the benefits of gravity body traction is a flat backboard attached to a fulcrum. The user lays on the board and anchors his feet to it. The user then can rotate the device to an inverted position by shifting his center of gravity to the other side of the fulcrum by raising his arms. However, the range of exercise maneuvers that are possible on this device is limited because the user remains attached to the board when he is in the inverted position.

A device that has eliminated the need for the backboard is a pair of ankle bracelets or boots disclosed in U.S. Pat. No. 3,380,447. These bracelets or boots are attached to the user's ankles, and have foam padding on the inside and metal on the outside. A hook on the anterior side of the ankle hooks over a bar one inch in diameter or less suspended several feet above the foundation surface. The user hooks the hook over the bar and hangs in the inverted position. He has considerable freedom of movement because only his ankles are attached to a stationary object. These boots are sometimes used in conjunction with the above-mentioned fulcrum apparatus.

Nevertheless, the ankle bracelets or boots have severe limitations in that many people who have some back problems have difficulty putting the boots on without assistance and many users find it impossible to raise their legs to the bar from which they intend to hang without some assistance. Additionally, it has been found that the pressure on the foot, ankle, and heel areas associated with the use of these ankle bracelets or boots causes discomfort in many users, and prevents long periods of use of the apparatus. Thus, many people are deprived of the full benefits of exercising in the inverted position.

SUMMARY OF THE INVENTION

The gravity traction and exercise apparatus of the invention comprises an upper frame supported above a foundation surface, a first padded foot binder attached to the upper frame, a pair of substantially parallel inclined tracks attached to the upper frame, and a second padded foot binder coupled to the tracks to travel along those tracks. The padded foot binders comprise opposed L-shaped plates having substantially horizontal portions and substantially vertical portions with padding covering the outer surface of each L-shaped plate. The upper frame is supported above the foundation surface by a support frame comprising four substantially vertical elements. A foot ladder comprising a plurality of substantially horizontal elements connects one pair of the vertical frame elements, and a pair of handholds is attached to the other vertical frame elements.

With such an apparatus, an exerciser can easily invert himself without assistance and can exercise in the inverted position without a backboard limiting his freedom of movement. Additionally, since the padded foot binders distribute the exerciser's weight over a large area of his feet and ankles, he can hang in the inverted position for longer periods of time than were possible with the apparatus of the prior art.

To exercise using the apparatus, the exerciser faces a foot ladder comprising a plurality of substantially horizontal bars arranged one above another; he grasps a pair of handholds; he then walks up the foot ladder while continuing to grasp the handholds. Then the exerciser puts his feet and ankles between a pair of foot binders and moves the binders toward one another to securely hold his ankles between the binders. After his ankles are securely held by the binders, he can release the handholds and hang freely.

DETAILED DESCRIPTION OF THE PREFERRED EMBODIMENTS

Figure 1:
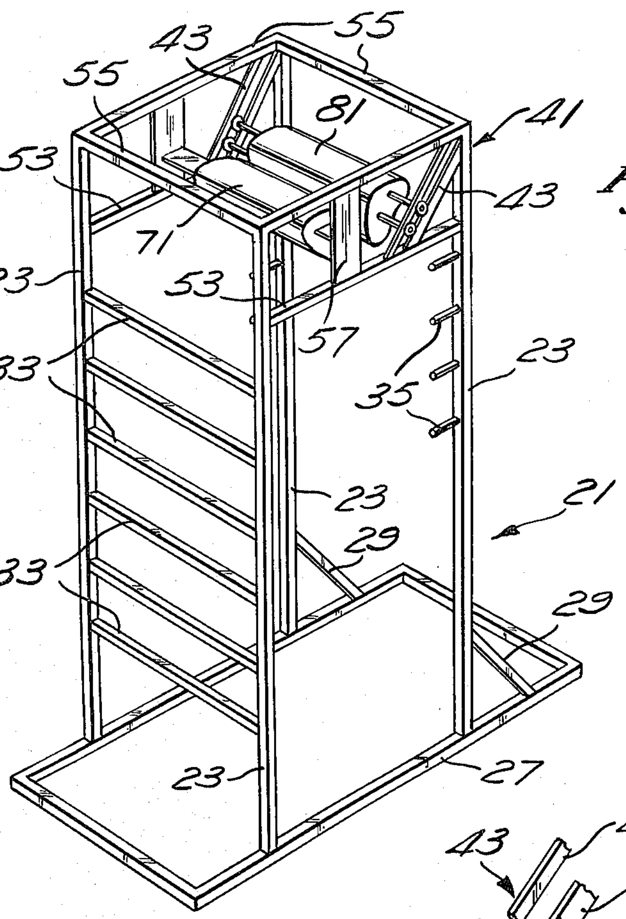
FIG. 1 is a perspective view of the gravity traction and exercise device of the present invention.

As shown in FIG. 1, the gravity traction and exercise apparatus comprises a lower frame 21 supporting an upper frame 41 a distance above a foundation surface. Coupled to the upper frame 41 are a first foot binder 71 and a second foot binder 81. The second foot binder 81 is movable along a pair of parallel inclined tracks 43.

THE FRAME

Referring to FIG. 1, the lower frame 21 includes a rectanguler base portion 27 that supports four vertical frame elements 23. The vertical frame members 23 are arranged to form a cuboid structure, approximately 32 inches per side. Diagonal support members 29 between two of the vertical elements 23 and the base 27 provide additional strength for the frame structure. The frame is advantageously formed of tubular steel, with the different frame elements welded together.

A foot ladder comprising substantially horizontal elements 33 is provided along one side of the lower frame 21. These horizontal foot bars 33 are connected between two adjacent vertical frame elements 23. The foot ladder elements 33 are placed one above the other to define a substantially vertical plane and are spaced approximately 6 inches to 1 foot apart.

Attached to the two vertical frame elements 23 opposite the foot ladder bars 33 are handholds 35. These handholds 35 are advantageously short (approximately 6 to 8 inches) horizontal bars directed toward the foot ladder elements 33. The lowest handholds 35 are best attached to the vertical frame elements 23 at a height of not more than 48 inches. Identical sets of handholds 35 are placed on each of the vertical frame elements 23 to which the horizontal foot elements 33 are not attached.

The lower frame 21 supports an upper frame 41 above the foundation surface. This upper frame 41 best includes horizontal elements 55 connecting the upper ends of the vertical frame elements 23 to provide increased structural rigidity. Parallel horizontal frame elements 53 extend between the vertical frame elements 23 to which the foot ladder elements 33 are attached and the vertical frame elements 23 to which the handholds 35 are attached.

Attached to the upper frame elements 53 are support members 57. The first foot binder 71 is attached to the support members 57.

Attached to elements of the upper frame 41 are a pair of parallel inclined tracks 43 that carry the second foot binder 81. The lower end of each of the tracks 43 is attached to one of the horizontal upper frame elements 53. The upper ends of the tracks 43 are advantageously attached to the vertical frame elements 23. The parallel tracks 43 are preferably angled at approximately 45 degrees.

Figure 2:
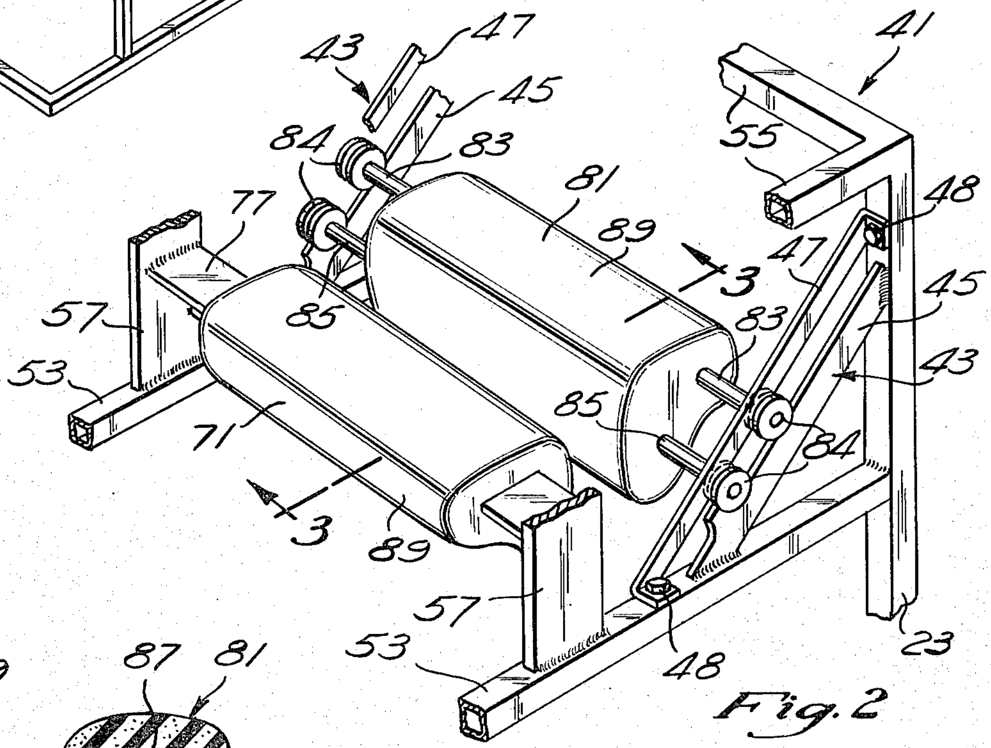
FIG. 2 is an enlarged, partially cut away view of the upper frame and the foot binders of the present invention.

Referring to FIG. 2, the details of the inclined tracks 43 will be described. Each track 43 comprises a lower track member 45 and an upper track member 47. The lower track member 45 and the upper track member 47 are spaced apart to allow room for the guide wheels 84 that are coupled to the second foot binder 81 to move between them. The upper track member 47 is preferably removably attached to the frame members 23 and 53 with bolts 48 so the upper track member 47 can be attached to the upper frame 41 after the second foot binder 81 with its guide wheels 84 is placed in position. Additionally, the use of removable bolts 48 permits the upper track member 47 to be removed so the second foot binder 81 can be removed from the apparatus for servicing or replacement.

The height of the entire frame, from the base 27 to the top upper frame horizontal elements 55 is approximately 7½ feet. The height of the lower frame 21 from the base 27 to the horizontal upper frame elements 53 is approximately 6 feet-8 inches. These heights may need to be increased if the apparatus is to accomodate exceptionally tall users to ensure they do not contact the foundation surface when they use the apparatus.

THE FOOT BINDERS 71 AND 81

As shown in FIG. 2, a pair of foot binders 71, 81 are coupled to the upper frame 41 so they can be moved from a first position in which they are adjacent one another (shown) to a second position in which they are remote from one another to provide a relatively large gap between them. Preferably, as seen in FIG. 2, the first foot binder 71 is affixed to the upper frame 41, while the second foot binder 81 is mounted to be movable with respect to the upper frame 41 and with respect to the first foot binder 71. Nevertheless, the first foot binder 71 could be coupled to inclined tracks in a manner similar to the coupling of the second foot binder 81 to the parallel inclined tracks 43. This would enable both foot binders 71, 81 to move with respect to each other and with respect to the upper frame 41.

Figure 3:
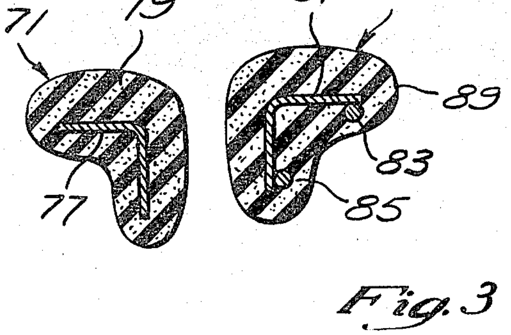
FIG. 3 is a cross-sectional view of the foot binders taken along line 3—3 of FIG. 2.

The first foot binder 71 comprises a L-shaped bar on plate 77 that is, in the preferred embodiment, affixed to support members 57, which are in turn attached to the horizontal upper frame elements 53. The L-shaped plate 77 has a horizontal portion and a vertical portion that extends downward from the horizontal portion. The outer surface of the plate 77, i.e., the upper surface of the horizontal portion and the right hand surface of the vertical portion as the plate 77 is viewed in FIG. 3, is covered with padding material 79. Advantageously, the padding material 79 extends all the way around the L-shaped plate 77, as shown in FIG. 3, to prevent injuries caused by sharp edges.

The second foot binder 81 similarly comprises a second L-shaped bar or plate 87 that has a horizontal portion and a vertical portion extending downward from the horizontal portion. A pair of horizontal mounting bars 83, 85 extend through the second foot binder 81 and are attached to the L-shaped plate 87. The ends of each of these horizontal support bars 83, 85 are coupled to the inclined tracks 43 by means of small mounting wheels 84, as shown in FIG. 2. These mounting wheels 84 permit the ends of the horizontal support bars 83, 85 to move up and down the inclined tracks 43 so the second foot binder 81 can move along an inclined path between a position adjacent the first foot binder 71 and a position remote from the first foot binder 71.

The L-shaped plate 87 of the second foot binder 81 is also covered with padding material 89 on its outer surface, i.e., the upper surface of the horizontal portion and the left hand surface of the vertical portion as shown in FIG. 3. Advantageously, the padding extends entirely around the L-shaped plate 87 to eliminate sharp edges that may cause injury.

The vertical portions of the first and second L-shaped plates 77 and 87 that form the first and second foot binders 71, 81 oppose one another across the opening between the two foot binders. As the angular position of the second foot binder 81 remains constant as the second foot binder 81 moves up and down along the inclined tracks 43, the opposed relationship of the vertical portions of the two L-shaped plates 77, 87 remains constant. This ensures that pressure is applied evenly to a user's ankles when they are placed between the first and second foot binders 71, 81.

Optionally, the padding 79 on the first foot binder 71 may be thinner and denser than the padding 89 on the second foot binder 81. When the user's instep, which bears most of his weight when he uses the apparatus, presses on the top of the second foot binder 81, the thicker, less dense padding 89 on that foot binder may, in some instances, provide greater comfort to the user. In contrast, as the posterior portion of the user's ankles and heels press against the first foot binder 71 with less force and bear less of the user's weight, a less deformable, denser padding material 79 may be adequate to cushion this portion of the ankle and foot.

Additionally, the padding 79, 89 on the first and second binders 71, 81 may be contoured so during use the padding fits closely around the user's ankles when the binders 71, 81 are closed onto the ankles.

The binders 71, 81 are preferably mounted on the upper frame 41 so a vertical plane passing between the first foot binder 71 and 81 the second foot binder 81, when the second binder is in its first, lower position, is closer to a substantially vertical plane that extends through handholds 35 (FIG. 1) than to the plane defined by the foot ladder elements 33.

USE OF THE APPARATUS

Referring to FIGS. 4, 5, 6, and 7, use of the apparatus by a person 91 having hands 93, a first foot 95, and a second foot 97 will now be explained. The user can easily invert himself with this apparatus without the assistance of another person.

Figure 4:
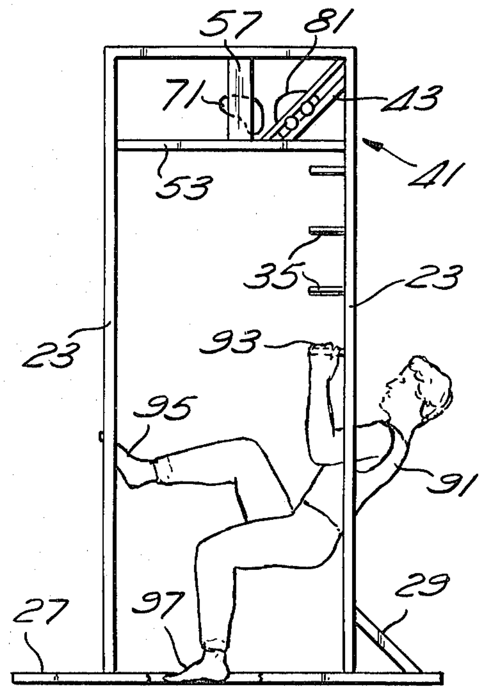
FIG. 4 is a side elevational view of the invention showing a user beginning to enter the apparatus.

Referring to FIG. 4, the user or exerciser 91 positions himself inside the cuboid apparatus between the two vertical elements 23 to which handholds 35 are attached, facing the foot ladder elements 33. He grasps the handholds 35 with his hands 93 and puts his first foot 95 up on one of the horizontal foot ladder elements 33 (FIG. 1). He then proceeds to place his feet 95, 97, on successively higher foot ladder rungs 33 to walk up the foot ladder and gradually invert his body as he holds onto the handholds 35 with his hands 93. Gravity holds the second binder 81 in its lower position on the tracks 43.

Figure 5:
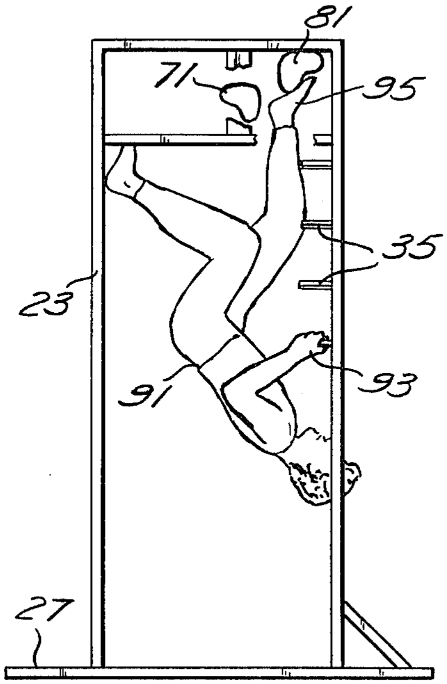
FIG. 5 is a view showing the user preparing to insert his feet between the foot binders.
Figure 6:
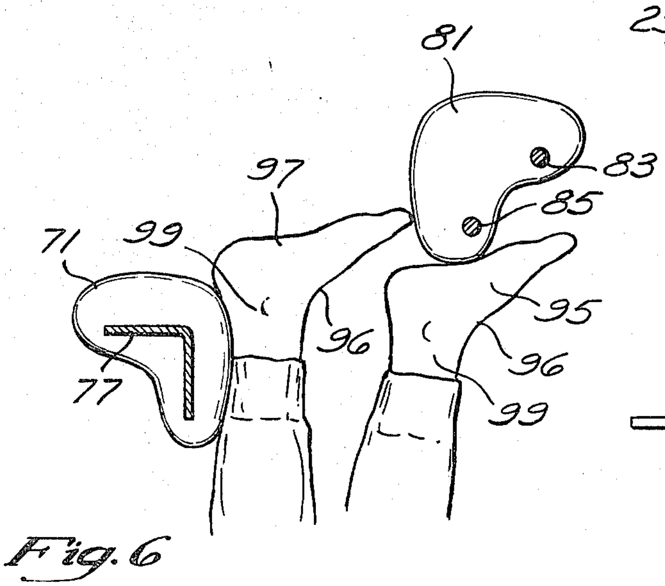
FIG. 6 is an enlarged view of the user's feet being inserted between the foot binders.

Referring now to FIG. 5, when the exerciser's feet have reached the top of the foot ladder, he uses his first foot 95 to push the second foot binder 81 up the inclined track 43 against gravity to its upper second position, remote from the first foot binder 71. He accomplishes this by pushing up on the bottom of the second foot binder 81 as shown in FIG. 6. This opens the space between the first foot binder 81 and the second foot binder 71. He then can insert his second foot 97 through the opening between the first foot binder 81 and the second foot binder 71. While holding the second foot binder up away from the first foot binder 71, such as by holding the toe of his second foot 97 against the second foot binder 81, he can then insert his first foot 95 through the opening between the two foot binders 71, 81.

Figure 7:
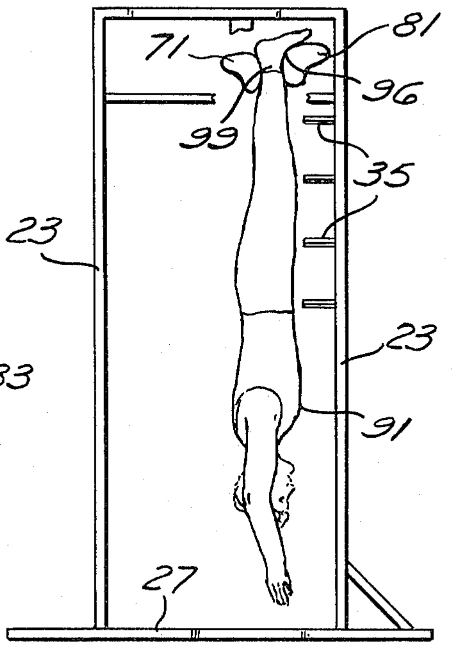
FIG. 7 is a view of the apparatus with the user in position in the apparatus.

Once the exerciser 91 has inserted both feet through the opening, while still holding onto the handholds 35, he moves his second foot 97 to release the second foot binder 81 so gravity moves it down the inclined track 43 until it presses against his ankles 99. Once the second foot binder 81 is in this position, the user's instep 96 is on top of the second foot binder 81 see (FIG. 7). The user 91 can then release his grip on the handholds 35 so his weight is applied through his instep 96 to the top of the second foot binder 81. This weight causes the second foot binder to be pulled farther down the inclined track 43 so it presses firmly against his ankles 99 and securely holds his ankles 99 between the first binder 71 and the second binder 81. Since the user's own weight closes the second foot binder 81 onto his ankles, the user 91 cannot slip out of the apparatus and fall.

Once the exerciser 91 is secured by his ankles in the apparatus he is able to hang free. He can perform a number of exercises, as he has complete freedom of movement of his body, except for his feet 95, 97 and ankles 99. He can thus do sit-ups, leg pulls, back arches and horizontal twists. He is not constrained by a back board.

The pressure on his feet 95, 97 and ankles 99 is distributed over a large area, so he is able to hang from the device for a longer period of time than is possible with the ankle bracelet or boot arrangement of the prior art, which concentrated the stress of the user's weight in a relatively small area of his feet. In the present apparatus, the exerciser's instep 96 presses against the padded top of the second binder 81. The padding 89 (see FIG. 3) distributes the exerciser's weight over the entire instep area 96 of the feet 95, 97, so the stress is not concentrated. As the exerciser's weight presses on the top of the second binder 81, it pushes the second binder 81 against his ankles 99, which in turn presses the opposite side of the user's ankles 99 against the first foot binder 71. The large padded surface of each of the binders 71, 81 distributes the pressure on both the front and rear of the ankles 99 over a relatively large area.

As discussed above, the binders 71, 81 are mounted on the apparatus so a vertical plane passing between them when the second binder 81 is in its lower position. When an exerciser 91 is using the apparatus, the second binder is in this lower position, firmly pressed against the exerciser's ankles 99. Thus, with the exerciser's body hanging in the apparatus facing away from the foot ladder, the user's body is closer to the handholds 35 to the foot ladder. This ensures that as the exerciser 91 performs his exercises parts of his body do not bump into the horizontal foot ladder elements 33. He can still move freely between the vertical elements 23 to which the handholds 35 are attached.

When the exerciser 91 becomes tired, he can again grasp the handholds 35 and pull himself back to the position in which his arms were supporting the majority of his weight. He then uses his ankles 99 to push the second foot binder 81 up the inclined track 43 and removes one foot at a time from between the two foot binders 71, 81 by reversing the procedure used to enter the apparatus. He can then walk down the foot ladder until his feet 95, 97 are on the foundation surface and release the handholds 35.

I claim:

1. An exercise device, comprising:
   - an upper frame supported a distance above a foundation surface;
   - a foot binding mechanism for holding the feet and ankles of a user to suspend the user in an inverted position, the foot binding mechanism comprising:
     - a first padded foot binder; and
     - a second padded foot binder, wherein the second foot binder is slidable along an inclined path defining an inclined plane from a position adjacent the first foot binder to a position remote from the first foot binder;
   - a foot ladder comprising a plurality of substantially horizontal elements defining a substantially vertical plane; and
   - a pair of handholds remote from the foot ladder;
   - wherein the first and second foot binders are situated above the foot ladder and the handholds and between the plane defined by the foot ladder and a substantially vertical plane passing through the handholds.

2. An exercise device, comprising:
   - an upper frame supported a distance above a foundation surface;
   - a foot binding mechanism for holding the feet and ankles of a user to suspend the user in an inverted position, the foot binding mechanism comprising:
     - a first padded foot binder coupled to the upper frame; and
     - a second padded foot binder movable between a first position substantially adjacent the first binder and a second position remote from the first binder, wherein the second foot binder is adapted to be firmly held in the first position by the weight of a user suspended by the foot binding mechanism;

a foot ladder comprising a plurality of substantially horizontal bars arranged one above another; and a pair of handholds;

wherein the upper frame is positioned above the foot ladder and above the handholds.

3. An exercise device, comprising:

a support frame comprising four substantially vertical elements;

a foot ladder comprising a plurality of substantially horizontal elements connecting two adjacent vertical elements;

a pair of handholds attached to the vertical elements not connected by the foot ladder;

an upper frame, comprising:

a first substantially horizontal upper frame element connecting one of the vertical frame elements to which the foot ladder is attached and one of the vertical elements to which a handhold is attached;

a second horizontal upper frame element connecting the other vertical element to which the foot ladder is attached and the other vertical element to which a handhold is attached;

a first inclined track attached to the first horizontal upper frame element;

a second inclined track, substantially parallel the first inclined track, attached to the second horizontal upper frame element;

a first padded bar coupled to the first horizontal support member; and a second padded bar coupled to the first and second inclined tracks.

4. The exercise device defined in claim 3, wherein:

the lower end of the first inclined track is attached to the first horizontal upper frame element relatively near the point at which the first padded bar is attached to the first horizontal upper frame element;

the lower end of the second inclined track is attached to the second horizontal upper frame element relatively near the point at which the first padded bar is attached to the second horizontal upper frame element.

5. The exercise device defined in claim 3, wherein:

the first padded bar comprises:

an elongate L-shaped plate having a horizontal portion and a vertical portion; and padding material covering the outer surface of the L-shaped plate; and the second padded bar comprises:

a pair of elongate rods, each of which is coupled to the first and second inclined tracks;

a second elongate L-shaped plate having a vertical portion and a horizontal portion, the second plate attached to the elongate rods; and padding material covering the outer surface of the second L-shaped plate.

6. An exercise device, comprising:

first and second substantially parallel inclined tracks;

a first foot binder for suspending a user in an inverted position, comprising:

a first plate; and padding covering an outer surface of the first plate;

a second foot binder, comprising:

a second plate having two outer surfaces substantially perpendicular each other; and padding covering the outer surfaces of the second plate;

wherein the padded surface of the first plate opposes one padded surface of the second plate; and support means attached to the second foot binder for coupling it to the inclined track so the second foot binder can move along a substantially inclined plane from a lower position adjacent the first foot binder to an upper position remote from the first foot binder, wherein when the user is in an inverted position his weight is substantially supported on the second outer surface of the second foot binder to hold the second foot binder in the lower position.

7. A method of exercising, comprising:

facing a foot ladder comprising a plurality of substantially horizontal bars arranged one above another;

grasping a pair of handholds;

placing a foot on one of the horizontal bars of the foot ladder;

walking up the ladder while continuing to grasp the handholds;

using one foot or both feet to separate a pair of binders;

placing a foot and ankle between the binders;

placing an instep against the top of one of the binders;

applying pressure to the top of the binder to move the binder down an inclined path to securely hold the ankle between the binders; and releasing the handholds.

8. A method of exercising, comprising:

facing a foot ladder comprising a plurality of substantially horizontal bars arranged one above another;

grasping a pair of handholds;

placing a foot on one of the horizontal bars of the foot ladder;

walking up the foot ladder while continuing to grasp the handhold;

placing a foot against one of the binders;

pushing a foot binder up an inclined track to move it away from another foot binder to open a space between the binders;

placing a foot and ankle between the pair of binders;

moving the binders toward each other to securely hold the ankle between the binders; and releasing the handholds.

9. An exercise device, comprising:

an upper frame supported a distance above a foundation surface; and a foot binding mechanism for holding the feet and ankles of a user to suspend the user in an inverted position, the foot binding mechanism comprising:

a first padded foot binder comprising an elongate L-shaped plate having a horizontal portion and a vertical portion, and padding material covering a surface of the L-shaped plate; and a second padded foot binder, comprising a second elongate L-shaped plate having a vertical portion and horizontal portion and padding material covering a surface of the L-shaped plate, wherein the second foot binder is slidable along an inclined path defining an inclined plane, from a position adjacent the first foot binder to a position remote from the first foot binder.

10. An exercise device, comprising:

an upper frame supported a distance above a foundation surface; and a foot binding mechanism for holding the feet and ankles of a user to suspend the user in an inverted position, the foot binding mechanism comprising:

a first padded foot binder coupled to the upper frame; and a second padded foot binder movable along a substantially inclined track coupled to the upper frame so the second padded foot binder is slidable along an inclined path defining an inclined plane from a position adjacent the first foot binder to a position remote from the first foot binder, wherein:

the first and second foot binders have substantially horizontal padded surfaces to support the exerciser's weight on the exerciser's instep and substantially vertical padded surfaces to limit movement of the exerciser's ankles.

* * * * *